US007943561B1

(12) United States Patent
Myers et al.

(10) Patent No.: US 7,943,561 B1
(45) Date of Patent: May 17, 2011

(54) HEAVY DUTY HAND CLEANER

(75) Inventors: E. Gary Myers, Payson, AZ (US); Leland M. Danzer, Chandler, AZ (US); Michael J. Couch, Phoenix, AZ (US)

(73) Assignee: The Dial Corporation, Scottsdale, AZ (US)

( * ) Notice: Subject to any disclaimer, the term of this patent is extended or adjusted under 35 U.S.C. 154(b) by 35 days.

(21) Appl. No.: 12/611,452

(22) Filed: Nov. 3, 2009

(51) Int. Cl.
*A61K 7/50* (2006.01)

(52) U.S. Cl. ........ 510/130; 510/138; 510/139; 510/159; 510/424; 510/463; 510/506

(58) Field of Classification Search ........................ None
See application file for complete search history.

(56) References Cited

U.S. PATENT DOCUMENTS

| | | | | |
|---|---|---|---|---|
| 5,441,666 | A | 8/1995 | Dotolo | |
| 5,661,119 | A | 8/1997 | Hersh et al. | |
| 6,376,437 | B2 | 4/2002 | Viscovitz et al. | |
| 6,533,873 | B1 | 3/2003 | Margosiak et al. | |
| 6,846,785 | B2 | 1/2005 | Patel | |
| 2004/0266645 | A1 * | 12/2004 | Albrecht et al. | 510/395 |

* cited by examiner

*Primary Examiner* — Necholus Ogden, Jr.
(74) *Attorney, Agent, or Firm* — Richard G. Hārrer

(57) ABSTRACT

A liquid hand cleansing composition which has the ability to remove stubborn soils such as ink, grease, paint and the like. The composition is also able to hold water insoluble particles in suspension without separation or sedimentation because of cooperation between a special suspension system and a surfactant system. Additionally, the composition remains homogenous and viscosity stabilized even in the presence of relatively large quantities of solvent such as d-limonene.

8 Claims, 1 Drawing Sheet

HEAVY DUTY HAND CLEANER

FIELD OF THE INVENTION

This invention pertains to liquid hand cleansing compositions which are considered to be heavy duty in the sense that they have the ability to remove stubborn soils such as ink, grease, paint and the like from the hands. Although the compositions have the ability to remove such soils, they are also basically non-irritating.

BACKGROUND OF THE INVENTION

Skin cleansing compositions are well known in the art and usually are used to clean the hands and arms of the user. Some skin cleansers are antibacterial in nature and are used to destroy microorganisms which might be present on a users hands. An example of such composition is disclosed in Taylor et al. (U.S. Pat. No. 6,616,922). However, most skin cleansing compositions are not very effective in removing heavy duty soils such as ink, grease, paint and the like from the hands. Also, a number of the compositions which are effective in removing such stubborn soils are not very mild to the skin and may cause irritation.

The prior art discloses hand cleansing compositions which are said to help in removing difficult soils. For example, U.S. Pat. No. 6,376,437 discloses a composition which is said to remove ink from the skin by incorporating a low molecular weight alcohol and a peroxide cleaning agent (i.e. sodium perborate) into the composition.

U.S. Pat. No. 5,441,666 discloses the incorporation of pumice into a composition to aid in the removal of soil from the hands. The composition also includes d-limonene, a C-11 alcohol ethoxylate as a detergent and an acrylic copolymer as an emulsifier.

Another heavy duty cleanser is described in U.S. Pat. No. 7,410,937 which discloses a composition which uses cornmeal as a scrubber. This is said to increase the cleansing efficiency by a mechanical effect. The composition also includes at least one ethoxylated fatty alcohol, an alkyl polyoxyethylene glycol, an alkanolamide and a polymeric quaternary ammonium salt.

U.S. Pat. No. 5,661,119 discloses a terpene based skin cleanser which includes up to 40% by weight of a terpene, a nonionic surfactant and cornmeal scrubbers.

Although not said to be a heavy duty hand cleanser, U.S. Pat. No. 6,846,785 discloses a liquid soap employing a base having an anionic surfactant, a chelating agent and an acrylic copolymer as a suspending agent. It is said that microcapsules are uniformly suspended in the liquid composition. The patent also discloses that such particles are usually suspended using Xanthan gum, although such a gum is not used in this particular soap composition.

U.S. Pat. No. 5,063,062 discloses a skin cleansing composition for removal of tar, adhesives and the like from the skin which employs from 5-60% by volume of orange oil, a moisturizer, and an oat grain derivative as an emulsifying agent.

SUMMARY OF THE INVENTION

This invention pertains to hand cleansing compositions which are considered as heavy duty in the sense that they have the ability to remove stubborn soils such as ink, grease, paint, and the like from the hands. Although the compositions have the ability to remove such soils, they are also basically non-irritating to the skin of most users. In a preferred composition according to this invention water insoluble particles to aid in soil removal are suspended in the composition without separation or sedimentation over time and this is achieved by employing a novel suspension system. In addition, the surfactant system used in the composition is such that it cooperates with the suspension system to cause the composition to better hold the insoluble particles in suspension.

Furthermore, the liquid cleansing compositions are formulated so the viscosity ranges from about 1,000 centipoises (cP) to about 20,000 centipoises. Viscosity is considered important in that as the viscosity approaches 1,000 cP the composition will tend to be more like water and difficult to remain on the hands during washing. If the viscosity is greater than about 20,000 cP the composition will be difficult if not impossible to dispense from containers having a hand pump or from wall mounted dispensers. Thus the hand cleansing compositions include:

A surfactant system which comprises:

an anionic surfactant such as sodium laureth sulfate an amphoteric surfactant, and an ethanolamide such as cocamide MEA or lauramide DEA A suspension system which comprises:

a diethanolamide or monoethanolamide such as cocamide MEA or lauramide DEA polymers such as Xanthan gum and "Veegum" which is a hydrated magnesium aluminum silicate ethoxylated glyceryl esters such as PEG-18-glyceryl/oleate/cocoate, and finely ground cereal grains such as oat grains Water insoluble exfoliating particles such as silica, ground apricot seeds or crushed walnut shells can also be used to aid in the removal of stubborn soils.

A solvent such as a citrus terpene is used to aid in the removal of greasy soil.

DETAILED DESCRIPTION OF THE INVENTION

Figure 1:
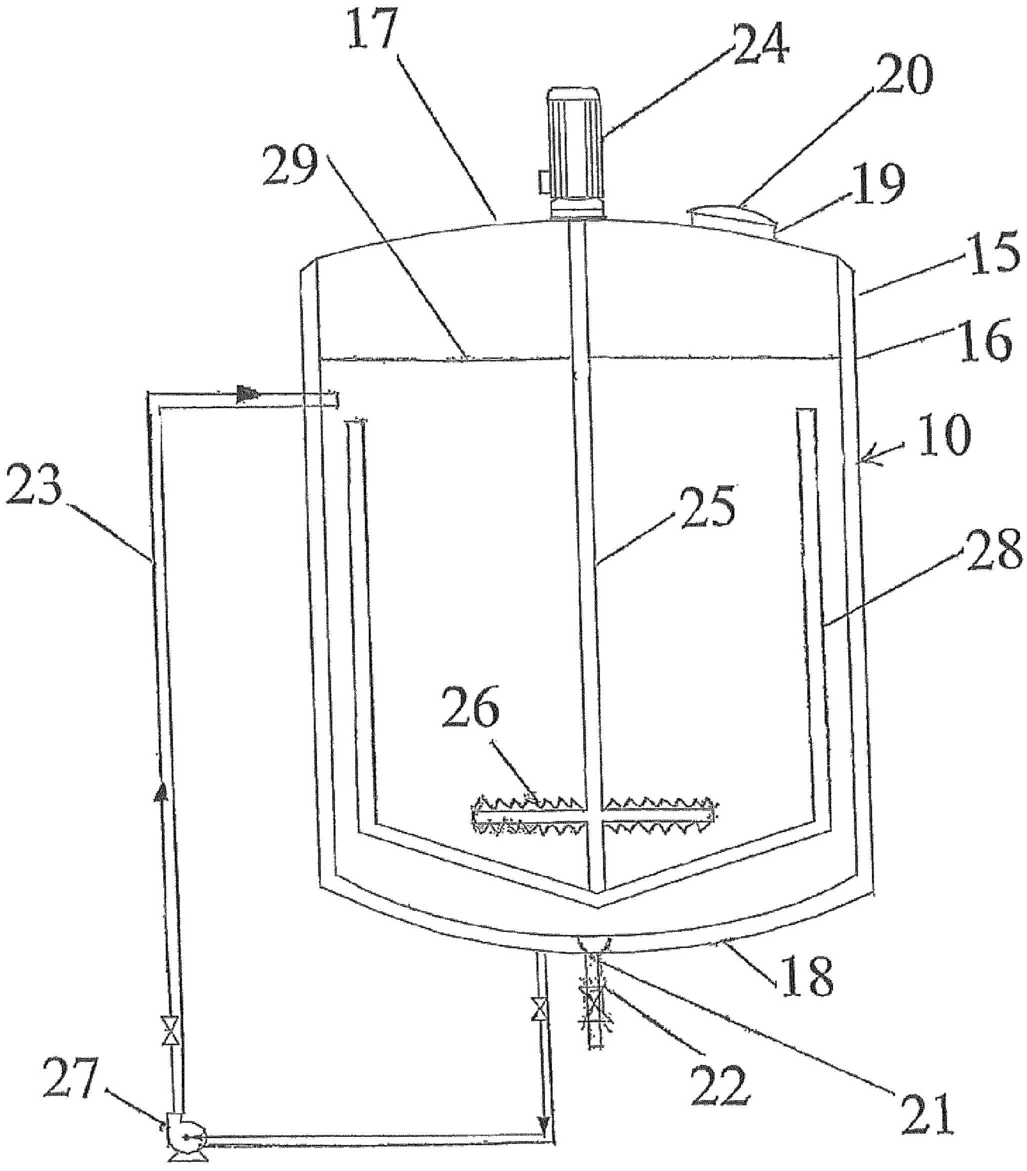
FIG. 1 is a side elevation view mainly in section of apparatus for mixing the ingredients making up the composition of the invention.

In one embodiment, this invention provides a liquid heavy duty aqueous hand cleansing composition capable of suspending water insoluble particles comprising:

About 5% to about 20% by weight of a surfactant system, said surfactant system further comprising:

a) about 4% to about 16% by weight of at least one anionic surfactant;

b) about 0.5% to about 6% by weight of an amphoteric surfactant;

c) about 0.1% to about 4% by weight of an ethanolamide.

About 4% to about 12% by weight of a particle suspension and thickening system, said particle suspension and thickening system comprising:

a) about 0.5% to about 4% by weight of a gum such as guar gum, locust bean gum, Xanthan gum, Veegum, and gum Arabic;

b) about 0.1% to about 4% by weight of an ethoxylated glyceryl ester such as PEG-18-glyceryl/oleate/cocoate;

c) about 0.1% to about 4% by weight of a monoethanolamide or diethanolamide such as cocamide MEA or lauramide DEA;

d) from about 0.95% to about 10% by weight of a finely ground cereal grain such as oats having a particle size ranging from about 25 to about 1000 microns.

About 1% to about 10% by weight of a solvent such as a citrus terpene to assist in the removal of oily soil.

About 0.01% to about 5% by weight of water insoluble particles such as silica to aid in the removal of stubborn soils.

Viscosity of the compositions range from about 1,000 centipoises to about 20,000 centipoises.

Surfactant System

With respect to the anionic surfactants useful in the surfactant system of this invention virtually all the anionics employed in skin cleansing preparations can be used. Suitable anionic surfactants include, for example, alkyl sulfates, alkyl ether sulfates, alkyl aryl sulfonates, alpha-olefin sulfonates, alkali metal or ammonium slats of alkyl sulfates, alkali metal or ammonium salts of alkyl ether sulfates, alkyl phosphates, silicone phosphates, alkyl glyceryl sulfonates, alkyl sulfosuccinates, alkyl taurates, acyl taurates, alkyl sarcosinates, acyl sarcosinates, sulfoacetates, alkyl phosphate esters, mono alkyl succinates, monoalkyl maleates, sulfoacetates, alkyl phosphate esters, mono alkyl succinates, monoalkyl maleates, sulfoacetates, acyl isethionates, alkyl carboxylates, phosphate esters, sulfosuccinates (e.g., sodium dioctylsulfosuccinate), and combinations thereof. Specific examples of anionic surfactants include sodium lauryl sulfate, sodium lauryl ether sulfate, ammonium lauryl sulfosuccinate, ammonium lauryl sulfate, ammonium lauryl ether sulfate, sodium dodecylbenzene sulfonate, triethanolamine dodecylbenzene sulfonate, sodium cocoyl isethionate, sodium lauroyl isethionate, sodium N-lauryl sarcosinate, and combinations thereof. The anionic surfactants that are most useful and preferred include alkyl sulfates and alkyl ether sulfates. These alkyl and alkyl ether sulfate surfactants correspond to the general formula $RO(C_2H_4O)_xSO_3M$ wherein R is an alkyl or alkenyl group of from about 8 to about 30 carbon atoms, x is about 0 to about 10 on average, and M is hydrogen or cation such as ammonium, alkanolammonium (e.g., triethanolammonium), a monovalent metal cation, such as sodium or potassium, or a polyvalent metal cation such as magnesium or calcium. Preferably, M should be chosen so that the anionic surfactant is water soluble.

Specific examples of the alkyl sulfates that can be used in the present invention are sodium lauryl sulfate and ammonium lauryl sulfate. Other preferred anionic surfactants are sodium lauryl ether sulfate (sodium laureth sulfate) and ammonium lauryl ether sulfate (ammonium laureth sulfate), preferably containing an average of from about 1 to about 4 or about 2 to about 3 moles of reacted (ring-open) ethylene oxides per molecule.

The amount of anionic surfactant in the surfactant system can range from about 4% to about 16% by weight of the composition, preferably from about 10% to about 14% by weight of the composition and most preferably about 12% by weight of the composition.

Another component of the surfactant system is an amphoteric surfactant. These surfactants are generally known for their surfactant activity and mildness. Amphoteric surfactants include betaines and real amphoteric surfactants based on fatty alkyl imidazolines. Betaines are characterized as having a fully quaternized nitrogen atom and the carboxylic group. It is preferred to use betaines, particularly the alkylamide betaines having the structure:

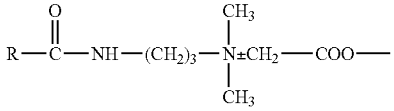

The most preferred betaines are those where R represents alkyl groups derived from coconut oil such as the cocoamidopropyl or the cocoamidoethyl betaines. Other suitable amphoteric surfactants include alkyl amphocarboxylates, which contain two nitrogen atoms, one or two carboxylate groups and an amide group having a relatively long chain alkyl or alkenyl group per molecule. These alkyl amphocarboxylates are sometimes referred to as "imidazoline" surfactants in the art.

The quantity of amphoteric surfactant in the surfactant system is from about 0.50% to about 10% by weight of the composition, preferably from about 1.5% to about 6%.

An additional component of the surfactant system and the suspension system as well is a fatty acid ethanolamide such as lauramide DEA (lauric diethanolamide), coconut fatty acid diethanolamide (cocamide DEA) or coconut fatty acid monoethanolamide (cocamide MEA) or lauric acid MEA (lauric monoethanolamide). These ethanolamides are nonionic and actually serve two purposes in the composition. They serve as a surfactant in the surfactant system and also are part of the particle suspension system to support or suspend the water insoluble particles in the composition. The quantity of the ethanolamide in the composition is from about 0.1% to about 4% of the composition, preferably from about 0.5% to about 1.5%.

Particle Suspension and Thickening System

The particle suspension and thickening system includes a finely ground cereal grain such as oat, barley, rice, wheat, corn, and the like. Finely ground oat protein is preferred and in the most preferable case is ground to a particle size of about 75 microns.

The particle size of the cereal grain such as oat grain is critical in that the size range should be adhered to otherwise the composition becomes "slimy". The particle size can range from about 25 to about 1000 microns, preferably about 75 microns. Preferably the amount of oat grain employed should be about 5% by weight of the composition. The total amount of cereal grain can range from about 0.95% by weight of the composition to about 10% by weight of the composition.

Another component of the suspension system is a gum such as guar gum, locust bean gum, Xanthan gum, Veegum, and gum Arabic. The amount of the gum present in the composition ranges from about 0.1% to about 4.0% by weight of the composition, preferably about 0.50%.

An additional component of the suspension system is an ethoxylated fatty acid ester. PEG-18 glyceryl/oleate/cocoate is particularly preferred since it serves not only an important function in the suspension system but it also serves to promote good skin feel. The amount of such esters can range from about 0.10% to about 4% by weight of the composition, preferably about 1% by weight of the composition.

Another component of the suspension system and the surfactant system as well is a fatty acid ethanolamide such as lauramide DEA (lauric diethanolamide), coconut fatty acid diethanolamide (cocamide DEA) or coconut fatty acid monoethanolamide (cocamide MEA) or lauric acid MEA (lauric monoethanolamide). These ethanolamides are nonionic and as previously noted serve two purposes in the composition. They serve as a surfactant in the surfactant system and also are part of the particle suspension system to support or suspend the water insoluble particles in the composition. It is believed that the inclusion of the non-ionic helps to solubilize the terpenes in the aqueous phase of the composition and therefore aides in preventing phase separation of the oil and water. The quantity of the ethanolamide in the composition is from about 0.1% to about 4% of the composition, preferably from about 0.5% to about 1.5%.

Solvent

To assist in the removal of greasy or oily soils, the composition of this invention includes a solvent suitable for use on human skin and the preferred solvent is a citrus terpene which is the major component of the oils extracted from citrus rind.

d-limonene is the major component of the oil extracted from citrus rind and is the preferred solvent. Orange terpene, lemon terpene and grapefruit terpene are also useful in the composition. The amount of the citrus terpene in the composition can range from about 1% to about 10% by weight of the composition, preferably about 4% to 6% by weight and most preferably about 6% by weight.

Exfoliating Particles

To aid in the removal of stubborn soils from the hands, a preferred embodiment employs from about 0.1% to about 5% by weight of the composition, preferably about 0.5% to about 3% of water insoluble exfoliating particles obtained from such sources as particles of ground apricot seeds, crushed walnut shells, coconut shells, almond seeds and shells, plant based materials such as jojoba, sawdust, polymers and inorganic particles such as sand, pumice, salt, alumina, silica, alumino-silicates, lava stone, and various phosphates. Additionally, ground corn cone can be used as a water-insoluble exfoliating particle (scrubber) if it's particle size is within the size ranges given below. Particle size of the water insoluble particles is important and can range from about 100 to about 400 microns, preferably from about 140 to 270 microns. Silica is the most preferred exfoliant in that it not only serves an exfoliating function but surprisingly serves to aid in suspending the water insoluble particles. Due to the powdery nature of the silica when present in the 100-400 micron size range, it helps to thicken the formula which in turn aides in the suspension of water insoluble exfoliants. It's presence in the composition also helps to prevent phase separation of the composition. These qualities of the silica occur at relatively low levels, that is about 0.70% by weight of the composition.

Viscosity

As earlier stated the viscosity of the composition is important and should range from about 1,000 to about 20,000 centipoises (cP). Preferably this viscosity should range from about 4,000 cP to about 6,000 cP and most preferably about 5,000 cP. The presence of a solvent, for example d-limonene in the composition impacts the viscosity of the composition in that increasing the amount of solvent reduces the viscosity of most heavy duty hand cleaning compositions. It has been discovered that the suspension system of this invention comprising the gums, ethoxylated glycerol esters, ethanolamides and finally ground cereals as well as the presence of the water insoluble particles such as silica allow the composition to easily contain up to 10% by weight of solvent without negatively impacting the viscosity. Thus, in the examples which follow the composition containing 3% by weight of solvent had a viscosity of 5540 cP, the composition containing 5% by weight of solvent had a viscosity of 4880 cP, the composition containing 6% by weight of solvent had a viscosity of 4810 cP, and the composition containing 8% by weight of solvent (orange terpene) had a viscosity of 5250 cP all within the preferred viscosity range.

It has also been observed with certain prior art compositions that the use of solvents such as d-limonene can cause the composition to separate into layers. With the compositions of this invention it has been discovered that relatively large amounts of solvent can be incorporated into the composition without separation into layers. It is believed that the presence of the oat grain and silica causes the composition to remain homogenous even in the presence of relatively large amounts of solvent. Thus the composition can easily tolerate up to about 10% by weight of solvent and remain homogenous.

EXAMPLES

Example 1

| Ingredient | % wt. |
|---|---|
| Sodium Laureth Sulfate | 12.5 |
| Cocoamidopropyl Betaine & Cocoamide MEA (Weight Ratio of Betaine to MEA is 4:1) | 3.3 |
| Orange Terpene | 5 |
| Fine Ground Oat Protein | 5.15 |
| Veegum K (Magnesium Alumina Silicate) | 1.4 |
| Xanthan Gum | .45 |
| Silica .70 | |
| Peg-18 Glycerol Oleate/Cocoate | 1.10 |
| Glycerin | 1.10 |
| Polyquaternium-7 | 0.55 |
| Triethanolamine | 0.40 |
| Borax 0.10 | |
| Preservatives | ~0.60 |
| Water to 100 | |
| Viscosity | 4880 cP |

Example 2

| Ingredient | % wt. |
|---|---|
| Sodium Laureth Sulfate | 12.0 |
| Cocoamidopropyl Betaine & Cocoamide MEA (Weight Ratio of Betaine to MEA is 4:1) | 3.2 |
| Orange Terpene | 3.0 |
| Fine Ground Oat Protein | 5.0 |
| Veegum K (Magnesium Alumina Silicate) | ~1.4 |
| Xanthan Gum | 0.50 |
| Ground Apricot Seeds | 1.0 |
| Peg-18 Glycerol Oleate/Cocoate | 1.0 |
| Glycerin | 1.0 |
| Triethanolamine | 0.40 |
| Borax 0.10 | |
| Preservative | ~0.60 |
| Water to 100 | |
| Viscosity | 5540 cP |

Example 3

| Ingredient | % wt. |
|---|---|
| Sodium Laureth Sulfate | 12.15 |
| Cocoamidopropyl Betaine & Cocoamide MEA (Weight Ratio of Betaine to MEA is 4:1) | 3.30 |
| Orange Terpene | 8.0 |
| Fine Ground Oat Protein | 5.15 |
| Veegum K (Magnesium Alumina Silicate) | 1.37 |
| Xanthan Gum | .45 |
| Silica .70 | |
| Peg-18 Glycerol Oleate/Cocoate | 1.10 |
| Glycerin | 1.10 |
| Polyquaternium-7 | 0.55 |
| Triethanolamine | 0.40 |
| Borax 0.10 | |

-continued

| Ingredient | % wt. |
|---|---|
| Preservatives | ~0.60 |
| Water to 100 | |
| Viscosity | 5250 cP |

In this example 3, it should be noted that even though the composition contained 8% by weight of solvent (orange terpene), the viscosity (5250 cP) was well within the desired range. Furthermore no separation into layers after storage was observed.

Example 4

| Ingredient | % wt. |
|---|---|
| Sodium Laureth Sulfate | 12.0 |
| Cocoamidopropyl Betaine & Cocoamide MEA | 3.20 |
| (Weight Ratio of Betaine to MEA is 4:1) | |
| Orange Terpene | 3 |
| Fine Ground Oat Protein | 5.0 |
| Veegum K (Magnesium Alumina Silicate) | 1.4 |
| Xanthan Gum | 0.50 |
| Ground Apricot Seeds | 1.00 |
| Peg-18 Glycerol Oleate/Cocoate | 1.00 |
| Glycerin | 1.00 |
| Polyquaternium-7 | 0.50 |
| Triethanolamine | 0.40 |
| Borax 0.10 | |
| Preservatives | ~0.60 |
| Water to 100 | |
| Viscosity | 3190 cP |

In example 4, it should be noted that even though the composition had a relatively low level of solvent (orange terpene) at 3%, the viscosity of the composition at 3190 cP was below the most desired range. It should also be noted that the composition used ground apricot seed as an exfoliant rather than the silica which was used in other of the examples. It is believed that the combination of the silica and the ground oat protein gives an unexpected result in providing both appropriate viscosity and homogeneity in the compositions.

Example 5

| Ingredient | % wt. |
|---|---|
| Sodium Laureth Sulfate | 12.0 |
| Cocoamidopropyl Betaine & Cocoamide MEA | 3.20 |
| (Weight Ratio of Betaine to MEA is 4:1) | |
| Orange Terpene | 6 |
| Fine Ground Oat Protein | 5.0 |
| Veegum K (Magnesium Alumina Silicate) | 1.4 |
| Xanthan Gum | 0.50 |
| Silica 0.70 | |
| Peg-18 Glycerol Oleate/Cocoate | 1.00 |
| Glycerin | 1.00 |
| Polyquaternium-7 | 0.50 |
| Triethanolamine | 0.40 |
| Borax 0.10 | |
| Preservatives | ~0.60 |
| Water to 100 | |
| Viscosity | 4810 cP |

Example 6

| Ingredient | % wt. |
|---|---|
| Sodium Laureth Sulfate | 12.0 |
| Cocoamidopropyl Betaine & Cocoamide MEA | 3.20 |
| (Weight Ratio of Betaine to.MEA is 4:1) | |
| Orange Terpene | 6.0 |
| Fine Ground Oat Protein | 5.0 |
| Veegum K (Magnesium Alumina Silicate) | 1.4 |
| Xanthan Gum | 0.50 |
| Scrubber: Silica | 0.70 |
| Scrubber: Corn Cone | 1.00 |
| Peg-18 Glycerol Oleate/Cocoate | 1.00 |
| Glycerin | 1.00 |
| Polyquaternium-7 | 0.50 |
| Triethanolamine | 0.40 |
| Borax 0.10 | |
| Preservatives | ~0.60 |
| Water to 100 | |
| Viscosity | 4580 cP |

METHOD OF PREPARING COMPOSITIONS

In order to provide a homogeneous composition which is not prone to separation the mixing apparatus shown in FIG. 1 was employed to prepare the compositions of this invention. As shown mixing apparatus 10 includes mixing vessel 15 which has a circular sidewall 16, bottom wall 18 and top 17. The top 17 of mixing vessel 15 is provided with a port 19 and a port cover 20. The bottom of mixing vessel 15 is provided with a threaded opening or drain 21 fitted with a shutoff valve 22. Recycle line 23 is directed into mixing vessel 15 through sidewall 16. Mounted on top of mixing vessel 15 is motor 24 which is operably connected to shaft 25. The lower end of shaft 25 is provided with a saw tooth dispersator blade 26. A side sweep 28 is attached to the end of shaft 25 and serves to aid in the mixing operation. To complete the mixing apparatus, centrifical circulation pump 27 is mounted in line 23 and returns product to the mixer through sidewall 16.

Mixing apparatus 10 is designed to provide a homogeneous composition which is not prone to separation. The liquids are first introduced into the vessel followed by the addition of powdered ingredients such as Veegum K, Xanthan gum, finely ground oat protein and silica. After all the ingredients are introduced into vessel 15, the mixing process begins with the mixer set at an rpm level high enough to pull a vortex for thorough mixing. The batch is recirculated by means of centrifical recirculation pump 27 pulling the mixture from the bottom of vessel 15 and returning it to the top portion of vessel 15 just below the fluid level 29 in the vessel. The saw tooth dispersator blade 26 and side sweep 28 all cooperate to help "wet-out" the powders and eliminate agglomerates leading to a homogeneous end product.

We claim:

1. A skin cleansing composition particularly adapted to remove stubborn soils from the hands of a user comprising:

a) from about 5% to about 20% by weight of a surfactant system, said surfactant system further comprising:

1) from about 4% to about 16% of at least one anionic surfactant;

2) from about 0.5% to about 6% of an amphoteric surfactant; and 3) from about 0.1% to about 4% of an ethanolamide;

b) from about 4% to about 12% by weight of a particle suspension system, said particle suspension system further comprising:
   1) from about 0.1% to about 4% of a gum;
   2) from about 0.1% to about 4% of an ethoxylated glyceryl ester;
   3) from about 0.1% to about 4% of an ethanolamide;
   4) from about 0.95% to about 10% of a ground cereal grain having a particle size ranging from about 25 to about 1,000 microns;
c) from about 1% to about 10% of a citrus terpene; and
d) from about 0.01% to about 5% of water insoluble exfoliating particles having a size ranging from about 100 to about 400 microns;
e) said composition having a viscosity of from about 1,000 centipoises to about 20,000 centipoises; and
f) wherein said ethanolamide serves as a component of the surfactant system and the suspension system and the total amount of said ethanolamide in said composition is from about 0.1% to about 4% by weight of the composition.

2. The composition of claim 1 wherein said anionic surfactant is an alkyl sulfate or alkyl ether sulfate corresponding to the general formula $RO(C_2H_4O)SO_3M$ wherein R is an alkyl or alkenyl group of from about 8 to about 30 carbon atoms, x is about 0 to about 10 on average, and M is hydrogen, ammonium, alkanolammonium, a monovalent metal cation such as sodium or potassium, or a polyvalent cation such as magnesium or calcium; said betaine is an alkylamide betaine corresponding to the general formula

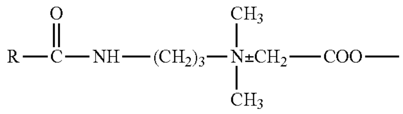

and said ethanolamide is a fatty acid ethanolamide.

3. The composition of claim 2 where said gum is selected from the group consisting of guar gum, locust bean gum, Xanthan gum, Veegum, and gum Arabic and wherein said cereal grain is about 5% by weight of the composition, and said water insoluble exfoliating particles range in size from about 100 to about 400 microns and are selected from the group consisting of particles of silica, ground corn cone, apricot seed and crushed walnut shells.

4. The composition of claim 3 wherein said cereal grain is oat grain and said exfoliating particles are ground silica having a particle size ranging from about 140 microns to about 270 microns and said composition has a viscosity of from about 4000 cP to about 6000 cP.

5. The composition of claim 3 wherein said ethoxylated glyceryl ester is PEG-18 glyceryl/oleate cocoate and said fatty acid ethanolamide is selected from the group consisting of lauramide DEA, cocamide DEA, and lauric acid MEA.

6. The composition of claim 5 wherein said citrus terpene is d-limonene and comprises from about 3% to about 8% by weight of said composition, said cereal grain has a particle size of about 75 microns and said water insoluble exfoliating particles comprise from about 0.5% to about 3% by weight of said composition.

7. The composition of claim 6 wherein said anionic comprises about 10% to about 14% by weight of said composition, said amphoteric comprises from about 1.5% to about 6% by weight of said composition and said ethanolamide comprises about 0.5% to about 1.5% by weight of said composition.

8. The composition of claim 7 wherein said anionic surfactant comprises about 12% to about 13% by weight of said composition, said ethoxylated glyceryl ester comprises about 1% by weight of the composition, said citrus terpene comprises about 6% by weight of said composition, said water insoluble exfoliating particles comprise from about 0.5% to about 1% by weight of said composition and the viscosity of said composition is about 5,000 cP.

* * * * *